United States Patent [19]

Efron et al.

[11] Patent Number: 5,705,172
[45] Date of Patent: Jan. 6, 1998

[54] COMPRESS COMPRISING MINERAL MUD

[75] Inventors: Dov Efron, Jerusalem; Zeev Maor, Dead Sea; Yohanan Furman, K. Maabarot, all of Israel

[73] Assignee: Dead Sea Laboratories Ltd., Israel

[21] Appl. No.: 596,501

[22] Filed: Feb. 5, 1996

[51] Int. Cl.$^6$ .......................... A01N 25/34; A61F 13/02; D04H 1/04

[52] U.S. Cl. .......................... 424/402; 424/443; 424/444; 424/445; 424/446; 604/291; 604/304

[58] Field of Search .................................. 604/291, 304; 428/80, 288, 296, 361, 394; 424/402, 443, 444, 445, 446

[56] References Cited

U.S. PATENT DOCUMENTS 4,900,377  2/1990  Redford et al. .................. 156/62.2
5,135,518  8/1992  Vera ................................ 604/291

*Primary Examiner*—Thurman K. Page
*Assistant Examiner*—Kathryne E. Shelborne
*Attorney, Agent, or Firm*—Nath & Associates; Gary M. Nath; Suet M. Chong

[57] ABSTRACT

The present invention relates to a compress comprising Dead Sea mineral mud or a mineral mud having similar properties. Said compress comprises substantially a fibrous cloth; an absorbent material on which a mineral mud having the properties of the Dead Sea mud is evenly spread; and a non permeable plastic sheet; all said layers being located one upon another; the materials being heat resistant to at least 70° C. and resistant to solutions of high salinity.

9 Claims, No Drawings

COMPRESS COMPRISING MINERAL MUD

BACKGROUND OF THE INVENTION

The present invention relates to a compress comprising Dead Sea mineral mud or a mineral mud having similar properties (hereinafter "the mud").

The invention will be described herein in particular with reference to Dead Sea mineral mud, however, it is not restricted to said mud. Thus, for example, certain muds obtained from the Tiberias Lake (Kinereth) may be used.

It is well known that mud mined from the Dead Sea has therapeutic effects in certain diseases when applied on the skin. However, the treatment with said mud has a drawback in that the patients have to come to the Dead Sea to receive their treatment. As is readily understood, this is quite expensive and it is difficult for many patients to come every time to receive the treatment on the shores of the Dead Sea.

There is known a package for the storage and use of Ahlenmoor. However, this package has a drawback that it requires the use of an additional heat carrier.

It has thus been desirable to design a device which overcomes the above drawbacks, and which can be readily used for the therapeutic treatment with the mud.

SUMMARY OF THE INVENTION

The present invention thus consists in a compress comprising the following layers, located one upon the other:

a) a porous fibrous cloth;

b) an absorbent material on which a mineral mud having the properties of the Dead Sea mud is evenly spread; and c) a non permeable plastic sheet, layers a) and c) extending to a small extent over layer b), and the edges of said layers a) and c) being bonded to each other; all said materials being heat resistant to at least 70° C. and resistant to solutions of high salinity.

DETAILED DESCRIPTION OF THE INVENTION

The porous fibrous cloth is suitably made of woven or non-woven cloth. Said cloth may be made, for example, of fibers of polymers, i.e. polypropylene, polyethylene; cellulose, cotton, etc.

The pores of said fibrous cloth should have a size which, on the one hand, prevents the migration of solid matter, and on the other hand allows the diffusion of certain liquid and soluble minerals.

Although any suitable mineral mud can be used, it has preferably the following parameters:

Particle size: 85%–smaller than 0.045 mm·pH: 6.0–8.0.
Water content: 18–38% (Loss on drying).
Water capacity: 0.7 g water/square cm.
Specific gravity: 1.2–2.0 g/cm square.
Chemical properties:
Total salinity: 8.0–33 g % w/w.
Composition of non soluble minerals—solid phase (60%):
Minerals, soluble in water—hallite (15–20%), aragonite.
Minerals, soluble in 10% HCl (carbonates)—calcite (25–35%), dolomite (20–25%), mica.
Minerals, non soluble in HCl (silicates)—quartz (10–15%), kaolinte, feldspar, montmorillonite.
Composition of soluble minerals—liquid phase (40%).
Major elements (typical values): chloride—70%, sodium—10%,
Magnesium—13%, calcium—6%, potassium—2.5%.
Trace elements:
strontium, sulphates, lithium, manganese, cooper, zinc, iron, nickle, cobalt, cadmium, plumbum, iodine, uranium, selenium and others.

The mud having the above parameters is obtained, for example, as follows:

a) Mud is mined on the shores of the Dead Sea and at the sediment of the Sea, in particular in the neighborhood of the river mouth.

b) The mud blocks are collected into ethanol pre-washed containers and covered immediately. The mud is transported to the plant area and covered with sterilized water, if needed. An anti bacterial agent is added to all mud containers.

c) Sieving (Sifting, Filtration) All machines and equipment are washed with ethanol before sieving. The mud is mixed to homogenization and consistency of about 40% water content. The suspension is shifted via two vibrated fraction screeners made of stainless steel:

1. The stainless steel screener consists of a sheet with pores of 0.5 cm for the removal of large particles, mainly crystals of hallite. Sieving is due to up and down movements of the screen.

2. Two sequential fraction screeners. The first is a porous stainless steel sheet with pores of 3 mm and the second is a stainless steel network with intervals of 0.5 mm. Sifting is due to vertical vibration of the screener.

The sieved mud is collected into ethanol pre-washed containers and immediately covered.

d) Sedimentation and final processing. The mud suspension is allowed to sediment until the desired consistency is achieved. The right consistency is obtained by removing, during the course of sedimentation, liquid that accumulated above the mud. The mud is being mixed with stabilizing agents, such as Bentonite and 0.1% Natrosol to homogenization and used for the manufacturing of the various articles.

The absorbent material is suitably a flexible cloth made of fibers with high swelling properties, i.e. non woven, made of viscosa fibers.

The non permeable plastic sheet should be resistant to the weight of the mud, be flexible and smooth, suitable for a thickness of 0.1–0.5 mm, be non permeable to salt solutions within the range of 8–35 g % w/w. It is, e.g. polyethylene (high and low density), polypropylene, P.V.C., etc.

The bonding of the edges of layers a) and c) may be performed, inter alia, in one of the following manners:

1. Welding by hot melting and subsequent cooling;

2. Gluing with a hot melt adhesive, e.g. Lunatack D 3376 C (H. B. Fuller).

3. Gluing with cold adhesive, e.g. Lunabond D 7077 (H. B. Fuller) The adhesive has to be resistant to mild heating conditions, such as oven at 60° C. degrees, immersing in water at 60° to 80° C. degrees and a short exposure to microwave radiation.

The compress is suitably manufactured as follows:

1. The various components, i.e. the permeable fibrous cloth, the absorbent material and the plastic sheets are cut to desired dimensions and shape.

2. Processed mud is being spread in an even manner on the absorbent material sheet. Alternatively the mud is spread continuously on a line of the absorbent sheet and the cutting takes place afterwards;

3. The layer of mud loaded absorbent material is laid on the non permeable plastic sheet and the surface of the mud layer is covered with the fibrous permeable cloth;

4. Bonding of the two opposite ends of layers a) and c) that are slightly larger than layer b) takes place by gluing or melting their ends together; and 5. The mud compress is folded to commercial units and packaged.

The dimensions of the compress according to the present invention are not critical features of the invention. They may be chosen according to the requirements of the patient, i.e. be adapted to the size of the body part to be treated with the compress.

When the compress is to be used it is advantageously heated to about 60° C. and put on the part to be treated therewith in such a manner that the porous fibrous cloth is located on said part.

It is readily understood that the compress according to the present invention overcomes the above drawbacks, and has several advantages, such as:

1. The treatment with the compress according to the present invention provides an improvement of the regular treatment by eliminating the dirt and the inconvenience of the regular mud packs treatment in which the mud is being applied directly on the skin. The facilities required for handling a treatment unit based on this device are much simpler.

2. The device is thermostable and can be heated before application on the skin, thus causing no bad feeling at the beginning of the treatment.

3. The device can be used by the patients themselves at home. Hence, the device can be defined as a "treat yourself" unit.

4. The device may be based on the assembly of the mineral mud with articles that are being used for babies and old people (diapers).

5. The device can be provided at various salts concentrations, consistencies and shape configurations.

The invention will now be illustrated with reference to the following Example, without being limited by same.

EXAMPLE

The compress was prepared in the manner described above.

It comprised:

a) Non woven porous polypropylene made by Shalag Industries 55×35 cm.

b) Non woven cloth of viscous fibers made by Gay Industries 50×30 cm. On said cloth were evenly spread 500 grams of the mud having the preferred properties set out above. Consistency 36% water content (loss on drying). Salinity 24 g % w/w total salt concentration.

c) High density polyethylene made by Plasmer Industries 55×30 cm.

The edges of layers a) and c) were glued together with strips of hot melt glue; 20×15 cm by heating for 30 seconds in a microwave.

Method of Application

The compress is pre-heated in a microwave and spread with the plastic layer down, on a bed covered with towel.

The patient is laid with his lower back on the non woven polypropylene of the mud compress for 20 minutes. At the end of the treatment the back is cleaned with a wet towel or with dry soft paper.

Recommended treatment course: 3 times a week for 4 weeks.

We claim:

1. A compress comprising the following layers located one upon the other:

a) a porous fibrous cloth having pores of a size which prevents migration of solid matter while allowing diffusion of liquid and soluble minerals;

b) an absorbent material on which a mineral mud having the properties of Dead Sea mud is evenly spread; and c) a non permeable plastic sheet, wherein said layers a) and c) extend to a small extent over layer b), and the edges of said layers a) and c) are bonded to each other; and all said layers are heat resistant to at least 70° C. and resistant to solutions of high salinity.

2. The compress according to claim 1, wherein the mineral mud is mineral Dead Sea mud.

3. The compress according to claim 1, wherein the mud is pre-treated.

4. The compress according to claim 1, wherein the porous fibrous cloth is made of woven or non-woven cloth.

5. The compress according to claim 4, wherein the cloth is made of fibers of polymers selected from the group consisting of polypropylene, polyethylene, cellulose and cotton.

6. The compress according to claim 1, wherein the absorbent material is a flexible cloth made of fibers with high swelling properties.

7. The compress according to claim 2, wherein the mud is pre-treated.

8. The compress according to claim 3, wherein the mud is pre-treated by sterilizing the mud, sifting the mud, forming a suspension of the sifted mud, and then forming a sediment thereof.

9. The compress according to claim 7, wherein the mud is pre-treated by sterilizing the mud, sifting the mud, forming a suspension of the sifted mud, and then forming a sediment thereof.

* * * * *

UNITED STATES PATENT AND TRADEMARK OFFICE
CERTIFICATE OF CORRECTION

PATENT NO. : 5,705,172
DATED : Jan. 6, 1998
INVENTOR(S) : Dov Efron, et al

It is certified that error appears in the above-identified patent and that said Letters Patent is hereby corrected as shown below:

Column 4, claim 1, line 1, after "layers", add a comma.

Column 4, claim 1, line 7, replace "Dead Sea" with -- particle size = 85% - smaller than 0.045 mm; pH = 6.0-8.0; water content = 18-38% (loss on drying); water capacity = 0.7 g water/square cm; specific gravity = 1.2-2.0 g/cm square; and total salinity =8.0-33 g% w/w.--

Signed and Sealed this

Twenty-first Day of April, 1998

Attest:

BRUCE LEHMAN

Attesting Officer

Commissioner of Patents and Trademarks